Figure 1:
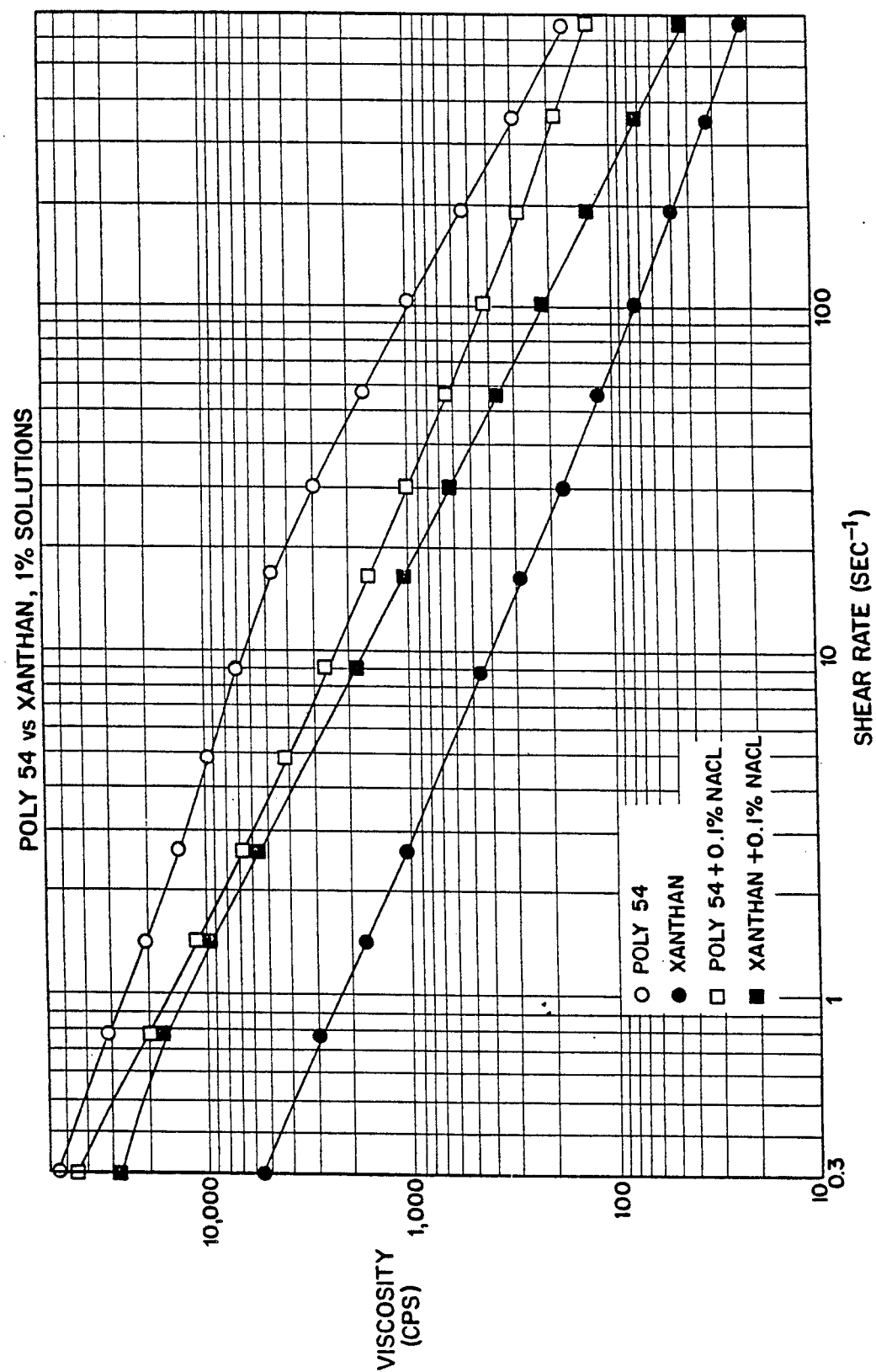

United States Patent [19]

Stirling

[11] Patent Number: 5,071,976
[45] Date of Patent: Dec. 10, 1991

[54] NOVEL HETEROPOLYSACCHARIDE

[75] Inventor: David I. Stirling, Fanwood, N.J.

[73] Assignee: Celgene Corporation, Warren, N.J.

[21] Appl. No.: 270,404

[22] Filed: Nov. 7, 1988

Related U.S. Application Data

[63] Continuation of Ser. No. 826,535, Feb. 6, 1986, abandoned, which is a continuation of Ser. No. 700,564, Feb. 11, 1985, abandoned.

[51] Int. Cl.$^5$ .................. C08B 37/00; C11P 19/04; C11N 1/20
[52] U.S. Cl. .................. 536/123; 435/101; 435/252.1
[58] Field of Search ............. 435/101, 252.1; 536/123

[56] References Cited

U.S. PATENT DOCUMENTS

| | | | |
|---|---|---|---|
| 3,346,463 | 10/1967 | Goren | 435/101 |
| 3,932,218 | 1/1976 | Finn et al. | 435/101 |
| 4,514,563 | 4/1985 | Fujiyama | 435/101 |
| 4,638,059 | 1/1987 | Sutherland | 536/121 |

FOREIGN PATENT DOCUMENTS 1589865  5/1981  United Kingdom.

OTHER PUBLICATIONS

Huq et al., *Aust. J. Biol.*, 1978, vol. 31, pp. 311–316.
Bergey's Manual, 8th ed., 1979, Williams & Wilkins (p. 268).
Colby et al., *Ann. Rev. Microbiol.*, 1979, vol. 33, pp. 481–517.
Byrom, D. in *Microbial Growth on $C_1$ Compounds*, H. Dalton. ed., 1981, pp. 278–289.
Hackh'3 s Chemical Dictionary, 4th Edition, McGraw-Hill, 1972.

*Primary Examiner*—D. W. Robinson
*Assistant Examiner*—Irene Marx
*Attorney, Agent, or Firm*—Mathews, Woodbridge, & Collins

[57] ABSTRACT

This invention provides a fermentation process which involves aerobically cultivating a strain of *Methylophilus viscogenes* under growth conditions to produce an accumulated quantity of a novel type of exopolysaccharide, such as heteropolysaccharide Poly 54.

3 Claims, 2 Drawing Sheets

NOVEL HETEROPOLYSACCHARIDE

CROSS-REFERENCE TO RELATED APPLICATIONS

This is a continuation of Ser. No. 06/826,535, filed Feb. 6, 1986 which is in turn a continuation-in-part of Ser. No. 06/700,564, filed Feb. 11, 1985, both now abandoned.

BACKGROUND OF THE INVENTION

In the last decade the production of single-cell protein(SCP) from $C_1$-compounds has been studied extensively both by academic and industrial laboratories. Enterprises such as Mitsubishi Gas Chemical Co., Hoechst, and I.C.I. have implemented pilot plant studies, but to date only I.C.I. is operating a full scale SCP plant. "Pruteen" is the registered trademark of the I.C.I. product and is made by the fermentation of the obligate methylotrophic bacterium, *Methylophilus methylotrophus*, which is eventually separated and dried to a powder or granules *Methylophilus methylotrophus* is an obligate methylotroph which uses the ribulose monophosphate pathway(RMP) cycle of formaldehyde fixation. *Methylophilus methylotrophus* kStrain AS-1 is a gram negative, nonpigmented rod with a single polar flagellum.

In SCP production, methanol feedstock constitutes the highest percentage of the operating costs, so that any increase in the microbial growth rate yield has a direct influence on the operating costs of the SCP production. For this reason I.C.I. has applied recombinant DNA technology to increase the cell yield by altering the genome of the *Methylophilus methylotrophus* microorganism. The genes for the more efficient glutamate dehydrogenase nitrogen assimilation system from *Escherichia coli* were cloned and inserted into a *Methylophilus methylotrophus* strain. This strain previously had its less efficient glutamate synthase nitrogen assimilation system blocked by means of DNA mutation, as described by J. Windass et in Nature, 287 396(1980).

Although methanol generally is viewed as a substrate for the production of single cell protein, the factors that qualify it for SCP manufacture also recommend methanol as a potential feedstock for the production of accumulated extracellular metabolites such as exopolysaccharides. A number of microbial processes for the conversion of methanol to value-added products have been described but generally these are low-volume/high-priced compounds such as aminoacids. Thus, J. Bolbot and C. Anthony in Proc. Soc. Gen. Microbial, 5, 43(1978) found that a pyruvate dehydrogenase lacking mutant of Pseudomonas AMI could accumulate the aminoacids alanine and valine during growth on methanol Y. Tani et al in Agric. Biol Chem., 42, 2275(1978) have described the production of up to 5.2 grams per liter of L-serine from methanol employing an *Arthrobacter globiformis* strain. Up to the present time there has not been any report of methanol bioconversion to a commodity type of bulk chemical.

Accordingly, it is an object of this invention to provide a fermentation process for the bioconversion of a $C_1$-compound to an accumulated quantity of extracellular metabolite.

It is another object of this invention to provide a rapid growth culture medium for bio-oxidation of a methanol substrate to an accumulated quantity of an exopolysaccharide.

It is another object of this invention to provide a novel facultative methylotroph species.

It is another object of this invention to provide methylotrophic microorganism strains having the identifying characteristics of strain ATCC 39893 .

It is a further object of this invention to provide a novel heteropolysaccharide which exhibits properties suitable for imparting pseudoplastic and thixotropic properties to aqueous solutions.

Other objects and advantages of the present invention shall become apparent from the accompanying description and examples.

DESCRIPTION OF THE INVENTION

One or more objects of the present invention are accomplished by the provision of novel strains of bacteria having identifying characteristics comprising:

(a) aerobic, gram-negative, rod-shaped, motile and polarly flagellated cells;

(b) methylotroph capable of assimilating methanol via the ribulose monophosphate pathway;

(c) capable of growth on fructose; and (d) optimal growth rate at a cultivation medium temperature of 30°-43° C.

Generally the novel bacterial strains of the present invention exhibit glucose dehydrogenase activity.

In another embodiment this invention provides a bacterial culture having the identifying characteristics of strain ATCC 39893, said culture being capable of aerobic bioconversion of methanol to an extracellular accumulation of heteropolysaccharide.

Subcultures of accession Number ATCC 39893 strain can be obtained upon request from the permanent microorganism collection of the American Type Culture Collection, 12301 Parklawn Drive, Rockville, Md. 20852. The microorganism deposition is in accordance with the requirements of the Budapest Treaty for the purpose of patent procedure.

The bacterial strains having the identifying characteristics of strain ATCC 39893 are not members of any of the known methylotrophic species such as *Methylophilus methylotrophus*. For purposes of taxonomic identification herein, the name *Methylophilus viscogenes* is assigned to the.. new facultative methylotroph species which includes bacterial strains having the identifying characteristics of strain ATCC 39893.

The term "methylotroph" as empolyed herein refers to a microorgansim which is capable of growing nonautotrophically on carbon compounds having one or more carbon atoms but no carbon-carbon bonds. "Autotrophic" refers to growth on a carbon dioxide substrate.

The term "facultative methylotroph" as employed herein refers to a methylotroph which is capable of growth on one or more heterotrophic substrates, e.g., fructose.

The term "$C_1$-compounds" as employed herein refers to organic compounds which do not contain any carbon-carbon bonds, such as methanol, formaldehyde, formate, formamide, carbon monoxide, dimethyl ether, methylamine, dimethylamine, trimethylamine and trimethylamine N-oxide.

The term "exopolysaccharide" as employed herein refers to a polysaccharide which accumulates as an extracellular metabolite in a fermentation medium, as exemplified by xanthan gum.

The term "heteropolysaccharide" as employed herein refers to a polysaccharide which is composed of at least two different kinds of monosaccharidic units, such as mannose and galactose.

The term "ribulose monophosphate pathway" (RMP) as employed herein refers to the biochemical cycle in which three molecules of formaldehyde are condensed to produce either one molecule of pyruvate or one molecule of dihydroxyacetone phosphate.

Biochemical literature relating to elucidation of the ribulose monophosphate pathway and its variations include Biochem. J., 144, 465(1974) by J. Strom et al; Sci. Prog., 62, 167 (1975) by C. Anthony; and Biochem. J., 148, 513(1975) by Colby et al.

The ribulose monophosphate pathway involves enzymes which include G-phosphogluconate dehydrase/-phospho-2-keto-3-digluconate aldolase; fructose diphosphate aldolase; glucose-6-phosphate dehydrogenase; 3-hexulose phosphate synthase; phosphofructokinase; phosphoglucoisomerase; phospho-3-hexulose isomerase; phosphoriboisomerase; ribulose-5-phosphate 3-epimerase; transaldolase; transketolase; sedoheptulose diphosphate aldolase; and sedoheptulose-1,4-diphosphatase.

The RMP cycle effectively condenses 3 molecules of formaldehyde with 3 molecules of ribulose 5-phosphate to form 3 molecules of fructose 6-phosphate, which in turn regenerates 3 molecules of ribulose 5-phosphate via the cycle with the overall production of one molecule of dihydroxyacetone phosphate or pyruvic acid. These metabolites function as substrates for cellular biosynthesis.

The two key enzymes of the cycle are envisioned to be hexulose phosphate synthase and hexulose phosphate isomerase, which are the enzymes responsible for condensing formaldehyde and ribulose 5-phosphate and converting the product to fructose 6-phosphate. These are two recognized variants of the RMP cycle, i.e., the fructose bisphosphate variant which gives rise to dihydroxyacetone phosphate, and the Entner-Doudoroff variant which produces pyruvic acid.

Species Methylophilus viscogenes

A series of isolations were conducted on samples of soil and water which originated in the operating vicinity of a methanol manufacturing plant in Bishop, Texas. The samples were screened for the presence of methanol-utilizing microorganisms.

A portion of each sample was inoculated into 250 ml Erlenmeyer flasks containing methanol (0.5% v/v) and an appropriate nutrient medium, e.g., the mineral salts(MS) medium illustrated in Table I, plus one gram per liter of ammonium chloride. The flasks were incubated at various temperatures ranging from 30° C. to 55° C. After detectable turbidity indicative of growth occurred, 2 ml samples were removed and employed to inoculate similar sterile flasks of medium. A number of subsequent subcultures were taken for each original sample, then the cultures were streaked out on medium agar plates to obtain single microorganism-derived colonies from which pure cultures of methanol-assimilating microorganisms were obtained. Strain AICC 39893 was isolated and obtained as a biologically pure culture in this manner.

Strains of Methylophilus viscogenes exhibit a novel combination of properties that distinguish them from other methylotrophic bacteria. A Methylophilus viscogenes bacterium such as strain ATCC 39893 is a type 1 facultative methylotroph which utilizes the ribulose monophosphate pathway of $C_1$ assimilation, and which typically has a growth rate doubling time of 1-3 hours at 35°-40° C.

Strain ATCC 39893 grows on methanol, fructose and glucose. In addition, it will grow on a wider variety of heterotropic substrates (e.g., succinate and pyruvate) when an exogenous energy supply in the form of formate or methanol is present. This is a property not previously described for any known microorganism. For purposes of identification, bacteria manifesting this phenomenon are herein termed "latent facultative methylotrophs".

Bacteria having the characteristics comprising those of strain ATCC 39893 are further identified by non-slimy growth of pale orange colonies on solid media. Another identifying characteristic of a strain ATCC 39893 type of methylotrophic bacterium is a hexulose phosphate synthase/hexulose phosphate isomerase activity (J. P. Van Dijken et al; FEMS. Microbiol. Lett., 4, 97, 1978) of at least about 400 nanomoles of NADH formed per minute per milligram of protein.

Another significant property of a strain ATCC 39893 type of facultative methylotroph is the ability to bioconvert a methanol substrate into an accumulated quantity of an exopolysaccharide which imparts pseudoplastic and thioxtropic properties to aqueous solutions. A strain ATCC 39893 bacterium is particularly unique in its ability to produce a large quantity of accumulated exopolysaccharide in the cultivation medium, in the presence or absence of cell growth and under a variety of culture conditions. A strain ATCC 39893 bacterium has the inherent ability to divert a large percentage of available carbon source to biosynthesis of an exopolysaccharide.

A further chacteristic of a strain ATCC 39893 type of bacteria is a non-logarithmic pattern of growth, as opposed to an exponential growth phase. A strain ATCC 39893 culture exhibits a natural metabolic dysfunction which prevents unrestricted logarithmic growth. When the fermentation medium is supplemented with a variety of growth factors such as vitamins, aminoacids, or yeast extract, the non-logarithmic growth is not affected.

A Methylophilus viscogenes strain can be cultured aerobically in a nutrient medium comprising a carbon source, nitrogen source, salts, and various growth promoters.

Suitable nitrogen sources include ammonium sulfate, ammonium chloride, ammonia, diammonium phosphate, ammonium nitrate, sodium nitrate, urea, corn steep liquor, casein, peptone yeast extract, meat extract, and the like.

Suitable mineral salts include calcium salts, magnesium salts, potassium salts, phosphate salts, iron salts, manganese salts, zinc salts, copper salts, and the like. Bacterial growth promoters include soy bean protein hydrolysate yeast extract, vitamins, and aminoacids.

Cultivation of the microorganism in the nutrient medium typically is conducted aerobically at a temperature of 35°-40° C. and a pH between about 6.7-7.1 by means of shaken or submerged cultivation.

Exopolysaccharide Production

Employing the cultivation conditions previously described, a present invention strain of Methylophilus viscogenes produces and accumulates an exopolysaccharide in a high concentration and with a high rate of carbon source utilization.

Strain ATCC 39893 is capable of producing the exopolysaccharide in an amount up to about 10 grams per liter, based on the culture medium, when methanol is used as the growth carbon source. The yield of exopolysaccharide typically will vary in the range between about 30-60 percent, based on the quantity of methanol utilized.

Accordingly, in another embodiment this invention provides a process for producing a heteropolysaccharide which comprises aerobically cultivating a strain of *Methylophilus viscogenes* in a nutrient medium containing a growth carbon source (e.g., a $C_1$-compound or fructose) to yield the heteropolysaccharide as an accumulated extracellular product.

In a further embodiment, this invention provides a process for producing a heteropolysaccharide which comprises aerobically cultivating *Methylophilus viscogenes* strain ATCC 39893 or a mutant thereof in a nutrient medium containing methanol as a growth carbon source to yield heteropolysaccharid Poly 54 as an accumulated extracellular product, and optionally recovering the said product from the culture medium.

After the completion of a fermentation run, the whole cells are removed from the broth by conventional means such as centrifugation, ultrafiltration or heat sterilization. The heteropolysaccharide is recovered from the supernatant by any convenient procedure such as freeze-drying, or precipitation with a water-soluble organic solvent, e.g., acetone, methanol, ethanol, and the like. Precipitation of the heteropolysaccharide can also be effected by treatment of the solution with a calcium salt.

The crude heteropolysaccharide can be redissolved in water, and the aqueous solution then subjected to dialysis and lyophilization to provide a purified product.

The novel heteropolysaccharide Poly 54 product has an average molecular weight in the range between about 800,000 and 1,500,000.

Heteropolysaccharide Poly 54 exhibits a 0.5% viscosity of 2100 cps at 12 RPM, as measured with Brookfield RVT Viscometer Spindle No. 4 at 25° C. An aqueous solution of heteropolysaccharide Poly 54 is colorless, transparent and exhibits pseudoplastic and thixotropic viscosity properties. The aqueous solution viscosity properties are stable at temperatures up to about 130° C., and at pH values up to about 12.

Under low shear rate conditions, heteropolysaccharide Poly 54 exhibits an apparent viscosity which typically is about 5-30 times that of commercial xanthan gum. The comparative viscosity properties of heteropolysaccharide Poly 54 and commerical xanthan gum (e.g., Kelzan) under shear conditions are illustrated in FIG. 1.

Figure 2:
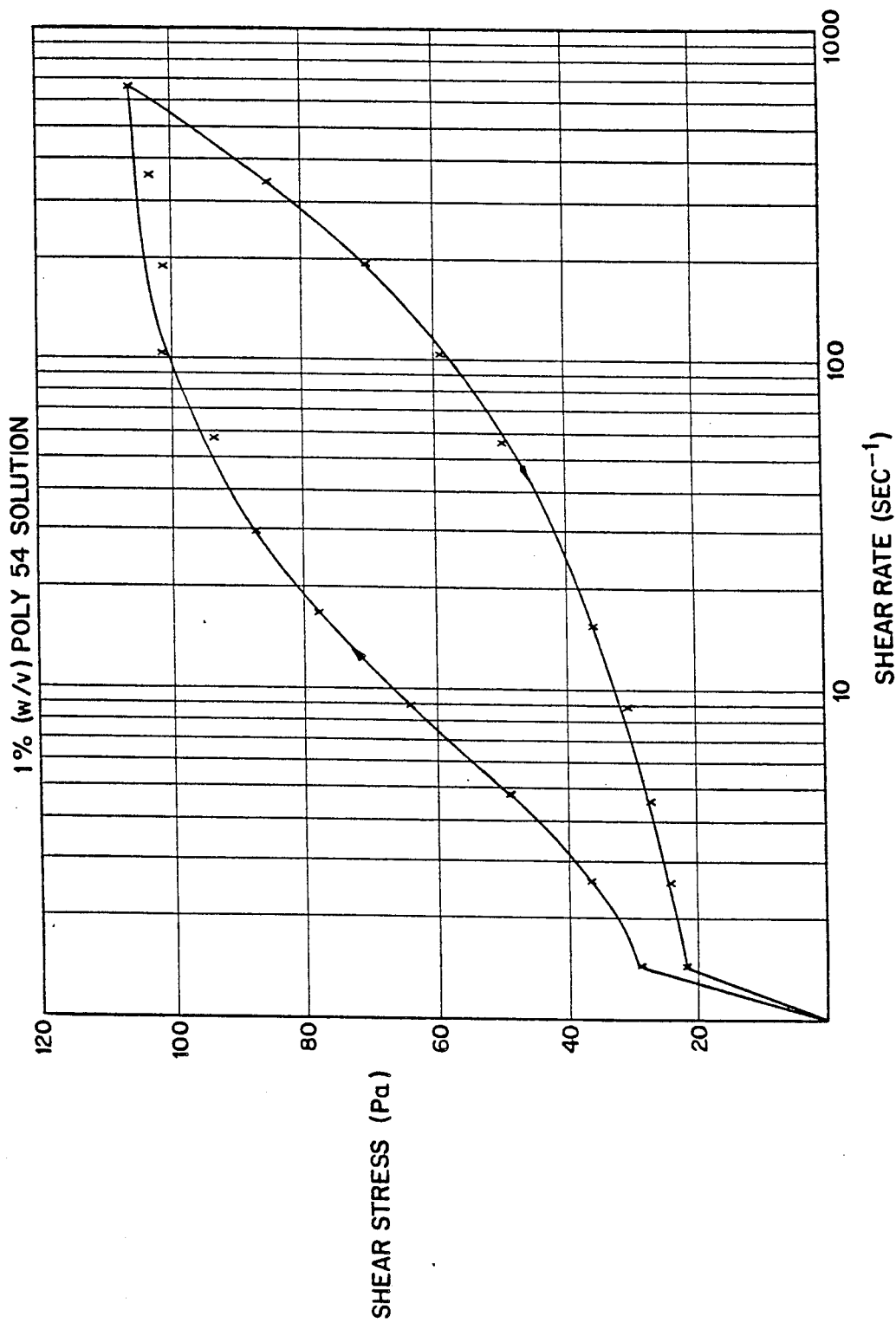

The pseudoplastic properties of an aqueous solution of heteropolysaccharide Poly 54 are illustrated in FIG. 2, which is a flow curve of 1%(W/V) Poly 54. The difference between the up curve and the down curve in FIG. 2 demonstrates that the polymer solution has thixotropic properties. Heteropolysaccharide Poly 54 has excellent properties for application as a thickening agent in aqueous solutions. Heteropolysaccharide Poly 54 can be employed alone or in combination with one or more other water-soluble polysaccharides such as hydrophilic gums. Illustrative of hydrophilic gums are xanthan gum and tamarind gum, and polygalactomannan gums such as guar gum and locust bean gum.

A synergistic enhancement of viscosity thickening effect in aqueous solutions is observed when heteropolysaccharide Poly 54 is utilized in combination with guar gum, locust bean gum, tara gum, starch or carboxymethylcellulose.

Other physicochemical and structural features of heteropolysaccharide Poly 54 are as follows:

| A. Constituent Sugars (molar ratio) | |
| --- | --- |
| glucose | 10 |
| galactose | 7-10 |
| mannose | 1-3 |
| uronic acid | 1-3 |

Poly 54 contains between about 1-3 weight percent of nitrogen. Poly 54 has no pyruvate or protein content, and it contains about one acetyl group per four monosaccharide units. The uronic acid constituent comprises glucuronic acid and/or galacturonic acid and/or mannuronic acid.

| B. Elemental Analysis (%)* | |
| --- | --- |
| C | 39.2 |
| H | 6.1 |
| O | 43.1 |
| N | 2.17 |

*Average values; ash corrected.

C. Melting Point

No clear melting point, and decomposes above a temperature of about 150° C.

D. Infrared Spectrum

Band at 1740 cm$^{-1}$ which may indicate aliphatic ester groups.

Bands at 1650 cm$^{-1}$ and 1540 cm$^{-1}$ which may indicate amide groups.

E. Ultraviolet Absorption Spectrum

No detectable peaks in ultraviolet range of wavelengths

F. Solubility Properties

Soluble in water, but insoluble in all common organic solvents.

G. Specific Rotation

No measurable specific rotation.

The present invention heteropolysaccharides differ in composition and properties from the polysaccharides described in U.S. Pat. No. 4,514,563. A polysaccharide of U.S. Pat. No. 4,514,563 is composed mainly of (a) glucose, (b) galactose, (c) mannose, and (d) glucuronic acid. The molar ratio of (a):(b):(c):(d) is 10:3-6:0.5-2:0-.5-2.

A typical polysaccharide of U.S. Pat. No. 4,514,563 is produced by an acetic acid bacteria such as *Acetobacter polysaccharogenes* MT-11-2 or MF-8. The polysaccharide does not contain acetyl or pyruvic acid constituents, and it does not contain any nitrogen. The viscosity of a 1% aqueous solution is 500-1200 centipoises as determined by a Brookfield type viscometer at 25° C. and a spindle rate of 30 revolutions per minute.

The following examples are further illustrative of the present invention. The components and specific ingredients are presented as being typical, and various modifications can be derived in view of the foregoing disclosure within the scope of the invention.

For growth of methanol-assimilating bacteria a mineral salts medium(MS) (Table I) is employed. The medium is either supplemented with 1 g/L potassium nitrate, giving nitrate mineral salts medium(NMS) or 1 g/L ammonium chloride, giving ammonium mineral salts medium (AMS). The carbon source, methanol, preferably is present at a concentration between 0.2–0.5%(v/v).

For solid media, 17 g/L of Difco bacto-agar is added to the basic mineral salts medium (minus phosphates) prior to sterilization. Sterile phosphate solution is added aseptically to the sterile mineral salts medium on cooling.

Fermentation procedures are conducted in a New Brunswick Microferm (14 liters). A 10 liter working volume is used, and methanol is added aseptically after sterilization of the fermentor. A stirring rate of 200 rpm is routinely used with an air delivery rate of two liters $m^{-1}$. The fermentor is equipped with pH and dissolved oxygen control.

Hexulose phosphate synthase/hexulose phosphate isomerase are assayed simultaneously, since there is no assay for hexulose 6-phosphate which is the product of hexulose phosphate synthase activity. Hexulose phosphate isomerase converts hexulose 6-phosphate to glucose 6-phosphate which can be estimated using glucose 6-phosphate dehydrogenase and following the concomitant $NADP^+$ reduction at 340 nm. The enzyme assay solution contains (final conc.): phosphate buffer 50 mM, pH 7.2; magnesium chloride 2.5 mM; glucose 6-phosphate dehydrogenase 0.7 units; phosphoglucoisomerase 0.75 units; phosphoribose isomerase 1.75 units; ribose 5-phosphate 5 mM; $NADP^+$ 0.25 mM; and formaldehyde 5 mM.

Any presence of hydroxypyruvate reductase is indicative of the serine pathway of formaldehyde assimilation in the microorganism. This is determined by an enzyme assay solution which contains (final conc.): potassium phosphate 1 M, pH 6.3; lithium hydroxy pyruvate 0.01 M; and NADH 2 mM. NADH disappearance is measured at 340 nm.

The estimation of glycerol and dihydroxyacetone is accomplished with glycerol dehydrogenase/dihydroxyacetone reductase (glycerol:$NAD^+$2-oxidoreductase, EC 1.1.1.6). The enzyme is derivated from *Enterobacter aerogenes*, and is available from Sigma Biochemicals.

For the estimation of glycerol, the reaction mixture (1.0 ml) contains 50 $\mu$mole TRIS-HCl buffer (Sigma Biochemicals), pH 9.7; 0.2 $\mu$mole $NAD^+$; 1 unit enzyme; and 15 $\mu$mole glycerol (or test solution/fermentation broth, 20–50 $\mu$l). Assays are initiated by addition of substrate and followed by monitoring increasing absorbance at 340 nm in a Beckman Model 25 UV spectrophotometer.

For the estimation of dihydroxyacetone, the reaction mixture (1.0 ml) contains 50 $\mu$mole phosphate buffer, pH 6.0; 0.5 $\mu$mole NADH; 1 unit enzyme; 15 $\mu$mole dihydroxyacetone (or test solution/fermentation broth, 20–50 $\mu$ml). Assays are initiated by addition of substrate and followed by monitoring decreasing absorbance at 340 nm.

The exopolysaccharide (e.g., heteropolysaccharide Poly 54) is recovered after the completion of a *Methylotrophus viscogenes* strain cultivation run. The broth is removed from the fermentor, and whole cells are removed by centrifugation (13,000 xg for 10 minutes). The exopolysaccharide usually is isolated by isopropanol precipitation from solution.

Rheological measurements on aqueous solutions of exopolysaccharides are made on a Wells/Brookfield cone/plate digital viscometer or a Rheomat 30 viscometer fitted with a coaxial cylinder sensor system.

The xanthan gum employed for comparative viscosity measurements is Kelzan, which is a commercial product sold by Kelco.

Analysis of the monosaccharide content of an exopolysaccharide is accomplished by a hydrolysis-gas liquid chromatography method. The method involves hydrolyzing the exopolysaccharide in aqueous trifluoroacetic acid solution, then reducing with sodium borohydride and acetylating with acetic anhydride. The polyacetate derivatives of the monosaccharides are then analyzed by gas chromatography in comparison to standards.

EXAMPLE

This Example illustrates the culturing of a *Methylophilis viscogenes* strain to form an accumulated quantity of exopolysaccharide metabolite.

A 500 ml inoculum of strain ATCC 39893 is grown employing MS medium, one gram per liter of ammonium chloride, and 0.5% (v/v) methanol as a growth carbon source. The flask is incubated at 37° C. for two days. A 14 liter New Brunswick Microferm fermentor containing 10 liters of MS medium, one gram per liter of ammonium chloride,.and 0.5% (v/v) methanol is inoculated with the above culture.

Initial fermentation conditions are as follows: 37° C., agitation 200 rpm, air flow 2 liters/minute, and pH 7.0. The pH is controlled at about 7.0 during the fermentation. Methanol is added intermittently to provide a concentration of 0.5% (v/v) whenever the fermentation medium becomes carbon exhausted. The concentration of methanol is determined by gas-liquid chromatography. After 24–36 hours of fermentation, the agitation rate is increased to 400 rpm.

The fermentation is terminated when methanol is no longer being utilized by the culture (usually 5–7 days) The highly viscous fermentation broth is then diluted with isopropanol (2:1 alcohol:broth) to facilitate precipitation of the exopolysaccharide. The resulting precipitate is filtered and then washed with 100% isopropanol, and then with 70% isopropanol. The precipitated exopolysaccharide is then dried at 55° C. in a forced air oven. The dried exopolysaccharide subsequently is ground to a powder in a Wiley Mill. The physicochemical properties of the exopolysaccharide product correspond to those described hereinabove for heteropolysaccharide Poly 54.

In an alternative process embodiment, heteropolysaccharide Poly 54 is recovered from a fermentation broth and purified in accordance with the following procedure.

At the termination of the fermentation, the fermentation broth is diluted 1:1 with deionized water and centrifuged at 10,000 revolutions per minute (rpm) for 20 minutes to separate microbial cells and solid materials. The broth then is dialyzed with deionized water for 72 hours with frequent changes of the water volume.

The addition of 2 volumes of isopropanol to the broth yields heteropolysaccharide Poly 54 as a white fibrous precipitate. The precipitate is collected, washed with isopropanol, and dried in a vacuum oven. The white precipitate is redissolved in deionized water and the solution is centrifuged as described above. The product is precipitated with isopropanol and then filtered and dried to produce purified heteropolysaccharide Poly 54.

TABLE I

| MS MEDIUM | |
|---|---|
| $MgSO_4.7H_2O$ | 1 g |
| $CaCl_2$ | 0.2 g |
| $Na_2HPO_4$ | 0.33 g |
| $KH_2PO_4$ | 0.26 g |
| FeEDTA | 5.0 mg |
| $Na_2MoO_4.2H_2O$ | 2.0 mg |
| $CuCl_2.2H_2O$ | 1.0 mg |
| $FeSO_4.7H_2O$ | 500 μg |
| $ZnSO_4.7H_2O$ | 400 μg |
| $MnCl_2.4H_2O$ | 20 μg |
| $H_3BO_4$ | 15 μg |
| $CoCl_2.6H_2O$ | 50 μg |
| $NiCl_2.6H_2O$ | 10 μg |
| EDTA | 250 μg |
| $H_2O$ | 1 liter pH 6.8 |

What is claimed is:

1. A heteropolysaccharide free of protein and containing (i) nitrogen in an amount of from about 1 to about 3 weight percent, (ii) as constituent monosaccharides, glucose, galactose, mannose, and at least one uronic acid selected from the group consisting of glucuronic acid, galaturonic acid, and mannuronic acid, the molar ratio of said constituent monosaccharides to one another being:

| | |
|---|---|
| glucose | 10 |
| galactose | 7 to 10 |
| mannose | 1 to 3 |
| uronic acid | 1 to 3. | and (iii) approximately one acetyl group for every four monosaccharides.

2. A thickening composition comprising a blend of a heteropolysaccharide according to claim 1 and at least one water soluble polysaccharide.

3. An aqueous solution of a composition according to claim 2.

* * * * *